(12) United States Patent
Nielsen

(10) Patent No.: US 8,486,003 B2
(45) Date of Patent: Jul. 16, 2013

(54) INSERTER HAVING TWO SPRINGS

(75) Inventor: Jens Egebjerg Nielsen, Ringsted (DK)

(73) Assignee: Unomedical A/S, Birkeroed (DK)

( * ) Notice: Subject to any disclaimer, the term of this patent is extended or adjusted under 35 U.S.C. 154(b) by 489 days.

(21) Appl. No.: 12/667,926

(22) PCT Filed: Jul. 2, 2008

(86) PCT No.: PCT/EP2008/058512
§ 371 (c)(1),
(2), (4) Date: May 14, 2010

(87) PCT Pub. No.: WO2009/007287
PCT Pub. Date: Jan. 15, 2009

(65) Prior Publication Data
US 2010/0228226 A1    Sep. 9, 2010

Related U.S. Application Data

(60) Provisional application No. 60/959,134, filed on Jul. 10, 2007.

(30) Foreign Application Priority Data

Jul. 10, 2007  (DK) .................................. 2007 01020

(51) Int. Cl.
*A61M 5/178*    (2006.01)
(52) U.S. Cl.
USPC ........................................... 604/36; 604/198
(58) Field of Classification Search
USPC ................... 604/134–137, 272, 274
See application file for complete search history.

(56) References Cited

U.S. PATENT DOCUMENTS

| | | | |
|---|---|---|---|
| 1,592,462 | A | 7/1926 | MacGregor |
| 2,047,010 | A | 7/1936 | Dickinson |
| 2,295,849 | A | 9/1942 | Kayden |
| 2,690,529 | A | 9/1954 | Lindblad |
| 2,972,779 | A | 2/1961 | Cowley |

(Continued)

FOREIGN PATENT DOCUMENTS

| | | |
|---|---|---|
| DE | 4 342 329 A1 | 6/1994 |
| DE | 196 31 921 A1 | 3/1997 |

(Continued)

OTHER PUBLICATIONS

International Search Report completed Sep. 26, 2008 for International Application No. PCT/EP2008/058512.

(Continued)

*Primary Examiner* — Kevin C Sirmons
*Assistant Examiner* — Brandy S Lee
(74) *Attorney, Agent, or Firm* — Brinks Hofer Gilson & Lione

(57) ABSTRACT

The invention relates to an inserter for a medical device e.g. an infusion set or the like for intermittent or continuous administration of a therapeutical substance, such as e.g. insulin. The inserter comprises a needle hub comprising an insertion needle and two elastic elements assuring automatic insertion and automatic retraction of the insertion needle. Activation of the first elastic element (11) cause a penetrating member (6A) to be inserted sub- or transcutaneously into the skin of a patient, and the second elastic element (12) cause the penetrating member (6A) to be retracted from the skin of the patient. The first elastic element (11) is in an unloaded state before activation and upon activation the first elastic element (11) energizes the second elastic element (12).

19 Claims, 11 Drawing Sheets

U.S. PATENT DOCUMENTS

| | | | |
|---|---|---|---|
| 3,059,802 A | 10/1962 | Mitchell | |
| 3,074,541 A | 1/1963 | Roehr | |
| 3,221,739 A | 12/1965 | Rosenthal | |
| 3,221,740 A | 12/1965 | Rosenthal | |
| 3,306,291 A | 2/1967 | Burke | |
| 3,485,352 A | 12/1969 | Pilger | |
| 3,509,879 A | 5/1970 | Bathish et al. | |
| 3,519,158 A | 7/1970 | Anderson | |
| 3,547,119 A | 12/1970 | Hall et al. | |
| 3,575,337 A | 4/1971 | Bernhardt | |
| 3,610,240 A | 10/1971 | Harautuneian | |
| 3,615,039 A | 10/1971 | Ward | |
| 3,670,727 A | 6/1972 | Reiterman | |
| 3,783,895 A | 1/1974 | Weichselbaum | |
| 3,788,374 A | 1/1974 | Saijo | |
| 3,810,469 A | 5/1974 | Hurschman | |
| 3,835,862 A | 9/1974 | Villari | |
| 3,840,011 A | 10/1974 | Wright | |
| 3,893,448 A | 7/1975 | Brantigan | |
| 3,937,219 A | 2/1976 | Karakashian | |
| 3,986,507 A | 10/1976 | Watt | |
| 3,986,508 A | 10/1976 | Barrington | |
| 3,995,518 A | 12/1976 | Spiroff | |
| 4,022,205 A | 5/1977 | Tenczar | |
| 4,188,950 A | 2/1980 | Wardlaw | |
| 4,201,406 A | 5/1980 | Dennehey et al. | |
| 4,227,528 A | 10/1980 | Wardlaw | |
| 4,259,276 A | 3/1981 | Rawlings | |
| 4,267,836 A | 5/1981 | Whitney et al. | |
| 4,296,786 A | 10/1981 | Brignola | |
| 4,315,505 A | 2/1982 | Crandall et al. | |
| 4,333,455 A | 6/1982 | Bodicky | |
| 4,334,551 A | 6/1982 | Pfister | |
| D267,199 S | 12/1982 | Koenig | |
| 4,378,015 A | 3/1983 | Wardlaw | |
| 4,402,407 A | 9/1983 | Maly | |
| 4,415,393 A | 11/1983 | Grimes | |
| 4,417,886 A | 11/1983 | Frankhouser et al. | |
| 4,464,178 A | 8/1984 | Dalton | |
| 4,473,369 A | 9/1984 | Lueders et al. | |
| 4,484,910 A | 11/1984 | Sarnoff et al. | |
| 4,500,312 A | 2/1985 | McFarlane | |
| 4,508,367 A | 4/1985 | Oreopoulos et al. | |
| 4,525,157 A | 6/1985 | Vaillancourt | |
| 4,530,695 A | 7/1985 | Phillips et al. | |
| 4,531,937 A | 7/1985 | Yates | |
| 4,543,088 A | 9/1985 | Bootman et al. | |
| 4,563,177 A | 1/1986 | Kamen | |
| 4,610,469 A | 9/1986 | Wolff-Mooij | |
| 4,617,019 A | 10/1986 | Fecht | |
| 4,713,059 A | 12/1987 | Bickelhaupt et al. | |
| 4,734,092 A | 3/1988 | Millerd | |
| 4,755,173 A | 7/1988 | Konopka et al. | |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,850,996 A | 7/1989 | Cree | |
| 4,863,016 A | 9/1989 | Fong et al. | |
| 4,878,897 A | 11/1989 | Katzin | |
| 4,890,608 A | 1/1990 | Steer | |
| 4,894,054 A | 1/1990 | Miskinyar | |
| 4,895,570 A | 1/1990 | Larkin | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,970,954 A | 11/1990 | Weir et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olson | |
| 5,020,665 A | 6/1991 | Bruno | |
| 5,024,662 A | 6/1991 | Menes et al. | |
| 5,067,496 A | 11/1991 | Eisele | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | van den Haak | |
| 5,116,325 A | 5/1992 | Paterson | |
| 5,121,751 A | 6/1992 | Panalletta | |
| 5,129,884 A | 7/1992 | Dysarz | |
| 5,135,502 A | 8/1992 | Koenig, Jr. et al. | |
| 5,137,516 A | 8/1992 | Rand et al. | |
| 5,137,524 A | 8/1992 | Lynn et al. | |
| 5,141,496 A | 8/1992 | Dalto et al. | |
| 5,147,375 A | 9/1992 | Sullivan et al. | |
| 5,163,915 A | 11/1992 | Holleron | |
| 5,172,808 A | 12/1992 | Bruno | |
| 5,176,643 A * | 1/1993 | Kramer et al. | 604/135 |
| 5,176,650 A | 1/1993 | Haining | |
| 5,176,662 A | 1/1993 | Bartholomew et al. | |
| 5,186,712 A | 2/1993 | Kelso et al. | |
| 5,188,611 A | 2/1993 | Orgain | |
| RE34,223 E | 4/1993 | Bonaldo | |
| 5,205,820 A | 4/1993 | Kriesel | |
| 5,222,947 A | 6/1993 | D'Amico | |
| 5,232,454 A | 8/1993 | Hollister | |
| 5,248,301 A | 9/1993 | Koenig et al. | |
| 5,256,149 A | 10/1993 | Banik et al. | |
| 5,256,152 A | 10/1993 | Marks | |
| 5,257,980 A | 11/1993 | Van Antwerp et al. | |
| 5,267,963 A | 12/1993 | Bachynsky | |
| 5,269,799 A | 12/1993 | Daniel | |
| 5,271,744 A | 12/1993 | Kramer et al. | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,344,007 A | 9/1994 | Nakamura et al. | |
| 5,350,392 A | 9/1994 | Purcell et al. | |
| 5,354,280 A | 10/1994 | Haber et al. | |
| 5,354,337 A | 10/1994 | Hoy | |
| 5,366,469 A | 11/1994 | Steg et al. | |
| 5,372,592 A | 12/1994 | Gambale | |
| 5,372,787 A | 12/1994 | Ritter | |
| 5,376,082 A | 12/1994 | Phelps | |
| 5,379,895 A | 1/1995 | Foslien | |
| 5,384,174 A | 1/1995 | Ward et al. | |
| 5,387,197 A | 2/1995 | Smith et al. | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,425,715 A | 6/1995 | Dalling et al. | |
| 5,429,607 A | 7/1995 | McPhee | |
| 5,429,613 A | 7/1995 | D'Amico | |
| 5,439,473 A | 8/1995 | Jorgensen | |
| D362,718 S | 9/1995 | Deily et al. | |
| 5,449,349 A | 9/1995 | Sallee et al. | |
| 5,451,210 A | 9/1995 | Kramer et al. | |
| 5,478,316 A | 12/1995 | Bitdinger et al. | |
| 5,490,841 A | 2/1996 | Landis | |
| 5,501,675 A | 3/1996 | Erskine | |
| 5,505,709 A | 4/1996 | Funderburk et al. | |
| 5,507,730 A | 4/1996 | Haber et al. | |
| 5,514,117 A | 5/1996 | Lynn | |
| 5,520,654 A | 5/1996 | Wahlberg | |
| 5,522,803 A | 6/1996 | Teissen-Simony | |
| 5,527,287 A | 6/1996 | Miskinyar et al. | |
| 5,533,974 A | 7/1996 | Gaba | |
| 5,540,709 A | 7/1996 | Ramel | |
| 5,545,143 A | 8/1996 | Fischell | |
| 5,545,152 A | 8/1996 | Funderburk et al. | |
| 5,549,577 A | 8/1996 | Siegel et al. | |
| 5,554,130 A | 9/1996 | McDonald et al. | |
| 5,558,650 A | 9/1996 | McPhee | |
| 5,562,629 A | 10/1996 | Haughton et al. | |

| | | |
|---|---|---|
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,379,335 B1 | 4/2002 | Rigon et al. |
| 6,387,076 B1 | 5/2002 | Van Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |

| | | |
|---|---|---|
| 6,923,791 B2 | 8/2005 | Douglas |
| 6,926,694 B2 | 8/2005 | Marano-Ford et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,850,652 B2 | 12/2010 | Liniger et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |

| | | | | | | |
|---|---|---|---|---|---|---|
| 2005/0119611 A1 | 6/2005 | Marano-Ford et al. | DE | 203 20 207 U1 | 11/2004 | |
| 2005/0119619 A1 | 6/2005 | Haining | EP | 0117632 B1 | 9/1984 | |
| 2005/0119637 A1 | 6/2005 | Lundgren et al. | EP | 0239244 B1 | 2/1987 | |
| 2005/0124936 A1 | 6/2005 | Mogensen et al. | EP | 0272530 A2 | 6/1988 | |
| 2005/0131347 A1 | 6/2005 | Marano-Ford et al. | EP | 0451040 A1 | 10/1991 | |
| 2005/0159709 A1 | 7/2005 | Wilkinson | EP | 0544837 B1 | 6/1993 | |
| 2005/0159714 A1 | 7/2005 | Gibson | EP | 0615768 A2 | 9/1994 | |
| 2005/0165382 A1 | 7/2005 | Fulford | EP | 0651662 B1 | 5/1995 | |
| 2005/0192560 A1 | 9/2005 | Walls et al. | EP | 0652027 A1 | 5/1995 | |
| 2005/0203461 A1 | 9/2005 | Flaherty et al. | EP | 0657184 A1 | 6/1995 | |
| 2005/0215979 A1 | 9/2005 | Kornerup et al. | EP | 0688232 B2 | 12/1995 | |
| 2005/0240154 A1 | 10/2005 | Mogensen et al. | EP | 0714631 B1 | 6/1996 | |
| 2005/0251098 A1 | 11/2005 | Wyss et al. | EP | 0744183 A2 | 11/1996 | |
| 2005/0256456 A1 | 11/2005 | Marano-Ford et al. | EP | 0747006 A1 | 12/1996 | |
| 2005/0261629 A1 | 11/2005 | Marano-Ford et al. | EP | 0799626 A1 | 10/1997 | |
| 2005/0277892 A1 | 12/2005 | Chen | EP | 0937475 A2 | 8/1999 | |
| 2005/0283114 A1 | 12/2005 | Bresina et al. | EP | 0956879 A1 | 11/1999 | |
| 2006/0015063 A1 | 1/2006 | Butikofer et al. | EP | 1086718 A1 | 3/2001 | |
| 2006/0015076 A1 | 1/2006 | Heinzerling et al. | EP | 1125593 A1 | 8/2001 | |
| 2006/0030815 A1 | 2/2006 | Csincsura et al. | EP | 0775501 B1 | 6/2002 | |
| 2006/0036214 A1 | 2/2006 | Mogensen et al. | EP | 1329233 B1 | 7/2003 | |
| 2006/0041224 A1 | 2/2006 | Jensen | EP | 1350537 A1 | 10/2003 | |
| 2006/0069351 A9 | 3/2006 | Safabash et al. | EP | 1360970 A1 | 11/2003 | |
| 2006/0069382 A1 | 3/2006 | Pedersen | EP | 1380315 A1 | 1/2004 | |
| 2006/0069383 A1 | 3/2006 | Bogaerts et al. | EP | 1407747 A1 | 4/2004 | |
| 2006/0095003 A1 | 5/2006 | Marano-Ford et al. | EP | 1407793 A1 | 4/2004 | |
| 2006/0095014 A1 | 5/2006 | Ethelfeld | EP | 1421968 A2 | 5/2004 | |
| 2006/0106346 A1 | 5/2006 | Sullivan et al. | EP | 1177802 B1 | 9/2004 | |
| 2006/0129123 A1 | 6/2006 | Wojcik | EP | 1475113 A1 | 11/2004 | |
| 2006/0135908 A1 | 6/2006 | Liniger et al. | EP | 1495775 A1 | 1/2005 | |
| 2006/0135913 A1 | 6/2006 | Ethelfeld | EP | 1502613 A1 | 2/2005 | |
| 2006/0142698 A1 | 6/2006 | Ethelfeld | EP | 1525873 A1 | 4/2005 | |
| 2006/0161108 A1 | 7/2006 | Mogensen et al. | EP | 1527792 A1 | 5/2005 | |
| 2006/0173410 A1 | 8/2006 | Moberg et al. | EP | 1559442 A2 | 8/2005 | |
| 2006/0173413 A1 | 8/2006 | Fan | EP | 1616594 A1 | 1/2006 | |
| 2006/0184104 A1 | 8/2006 | Cheney, II et al. | EP | 1704889 A1 | 9/2006 | |
| 2006/0184140 A1 | 8/2006 | Okiyama | EP | 1719537 A2 | 11/2006 | |
| 2006/0200073 A1 | 9/2006 | Radmer et al. | EP | 1762259 A1 | 3/2007 | |
| 2006/0241551 A1 | 10/2006 | Lynch et al. | EP | 1764125 A1 | 3/2007 | |
| 2006/0247553 A1 | 11/2006 | Diermann et al. | EP | 1776980 A1 | 4/2007 | |
| 2006/0247574 A1 | 11/2006 | Maule et al. | EP | 1970091 A1 | 9/2008 | |
| 2006/0253085 A1 | 11/2006 | Geismar et al. | FR | 2725902 A1 | 10/1994 | |
| 2006/0253086 A1 | 11/2006 | Moberg et al. | FR | 2 752 164 A1 | 2/1998 | |
| 2006/0264835 A1 | 11/2006 | Nielsen et al. | GB | 906574 | 9/1962 | |
| 2006/0264890 A1 | 11/2006 | Moberg et al. | GB | 2 088 215 A | 6/1982 | |
| 2007/0005017 A1 | 1/2007 | Alchas et al. | GB | 2 230 702 A | 10/1990 | |
| 2007/0016129 A1 | 1/2007 | Liniger et al. | GB | 2 423 267 A | 8/2006 | |
| 2007/0016159 A1 | 1/2007 | Sparholt et al. | GB | 2 450 872 A | 7/2007 | |
| 2007/0021729 A1 | 1/2007 | Mogensen et al. | JP | 10179734 A | 8/1991 | |
| 2007/0049865 A1 | 3/2007 | Radmer et al. | JP | 7051251 A | 11/1995 | |
| 2007/0049870 A1 | 3/2007 | Gray et al. | JP | 8187286 A | 7/1996 | |
| 2007/0051784 A1 | 3/2007 | Money et al. | JP | A-03-191965 | 7/1998 | |
| 2007/0066955 A1 | 3/2007 | Sparholt et al. | JP | 2002-028246 A | 1/2002 | |
| 2007/0088271 A1 | 4/2007 | Richards et al. | RU | 933 100 | 6/1982 | |
| 2007/0093754 A1 | 4/2007 | Mogensen | RU | 2 238 111 C2 | 12/2003 | |
| 2007/0104596 A1 | 5/2007 | Preuthun et al. | WO | WO 81/01795 A1 | 7/1981 | |
| 2007/0112301 A1 | 5/2007 | Preuthun et al. | WO | WO 82/03558 A1 | 10/1982 | |
| 2007/0112303 A1 | 5/2007 | Liniger | WO | WO 92/04062 A1 | 3/1992 | |
| 2007/0129688 A1 | 6/2007 | Scheurer et al. | WO | WO 93/05840 A2 | 4/1993 | |
| 2007/0173767 A1 | 7/2007 | Lynch et al. | WO | WO 93/11709 A1 | 6/1993 | |
| 2007/0179444 A1 | 8/2007 | Causey et al. | WO | WO 94/20160 A1 | 9/1994 | |
| 2007/0185441 A1 | 8/2007 | Fangrow, Jr. | WO | WO 95/19194 A1 | 7/1995 | |
| 2007/0191772 A1 | 8/2007 | Wojcik | WO | WO 96/32981 A1 | 7/1996 | |
| 2007/0191773 A1 | 8/2007 | Wojcik | WO | WO 96/20021 A1 | 10/1996 | |
| 2007/0203454 A1 | 8/2007 | Shermer et al. | WO | WO 98/26835 A1 | 1/1998 | |
| 2007/0213673 A1 | 9/2007 | Douglas | WO | WO 98/33549 A1 | 8/1998 | |
| 2007/0244448 A1 | 10/2007 | Lastovich et al. | WO | WO 98/58693 A1 | 12/1998 | |
| 2008/0269687 A1 | 10/2008 | Chong et al. | WO | WO 99/07435 A1 | 2/1999 | |
| 2008/0312601 A1 | 12/2008 | Cane' | WO | WO99/22789 A1 | 5/1999 | |
| 2009/0062767 A1 | 3/2009 | Van Antwerp et al. | WO | WO 99/33504 A1 | 7/1999 | |
| 2009/0326456 A1 | 12/2009 | Cross et al. | WO | WO 00/02614 A1 | 1/2000 | |
| 2010/0004597 A1 | 1/2010 | Gyrn et al. | WO | WO 00/03757 A1 | 1/2000 | |
| 2010/0137829 A1 | 6/2010 | Nielsen et al. | WO | WO 00/44324 A1 | 8/2000 | |
| 2010/0228226 A1 | 9/2010 | Nielsen | WO | WO 01/12746 A1 | 2/2001 | |
| 2010/0262078 A1 | 10/2010 | Blomquist | WO | WO 01/30419 A2 | 5/2001 | |
| | | | WO | WO 01/68180 A1 | 9/2001 | |
| FOREIGN PATENT DOCUMENTS | | | WO | WO 01/72353 A2 | 10/2001 | |
| DE | 299 05 072 U1 | 9/1999 | WO | WO 01/76684 A1 | 10/2001 | |
| DE | 101 17 285 A1 | 11/2002 | WO | WO 01/93926 A2 | 12/2001 | |

| | | | |
|---|---|---|---|
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO/2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO/2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/112521 A1 | 10/2010 |
| WO | WO 2011/012465 A1 | 2/2011 |
| WO | WO 2011/015659 A1 | 2/2011 |

OTHER PUBLICATIONS

International Preliminary Report on Patentability completed Oct. 20, 2009 for International Application No. PCT/EP2008/058512.
"Why inset®?" inset® infusion set product overview; http://web.archive.org/web/20040906102448/http://www.infusion-set.com/Default.asp?ID=108; two pages.

\* cited by examiner

INSERTER HAVING TWO SPRINGS

This application claims the benefit under 35 U.S.C. §371 of International Application No. PCT/EP2008/058512, filed Jul. 2, 2008, which claims the benefit of Danish Patent Application No. PA 2007 01020, filed Jul. 10, 2007, and U.S. Provisional Application Ser. No. 60/959,134, filed Jul. 10, 2007, which are incorporated herein in their entirety.

TECHNICAL FIELD

The invention relates to an inserter for a medical device e.g. an infusion set or the like for intermittent or continuous administration of a therapeutical substance, such as e.g. insulin. The inserter comprises a needle hub comprising an insertion needle and two elastic elements assuring automatic insertion and automatic retraction of the insertion needle.

BACKGROUND OF THE INVENTION

WO 2005/046780 (FIGS. 97-102) describes a device used for automatic insertion of a cannula of an infusion device into the skin of a patient, and afterwards automatic retraction of the insertion needle. The insertion device has the form of an oblong cylinder which is open in one end (1984) and provided with means for activation at the other end (1952). When the infusion set has been loaded onto the needle (1968) the lock member (1962) is moved in direction of the end provided with means for activation by the patient using projections (1974) until barbs (1956) of the lock member (1962) engage an outer surface of the housing (page 26, l. 24-27). The projections (1974) are accessible through a slot (1976) of the housing. Then the open end (1984) is placed against the skin of the patient and the means for activation (1952) is activated. When activated shoulders (1954) on the means for activation engage, the barbs (1956) are pushed toward each other in order to disengage the barbs from the housing. When the barbs are clear of the housing the lock member, the needle hub, the retainer body and the associated infusion device are moved by a first spring in direction of the open end (1984). The inserter device moves the infusion device towards the skin of the patient thereby inserting the needle and the cannula of the infusion device. As the cannula is fully inserted, barbs (1964) of the needle hub (1965) engage ramped surfaces (1972) of the sleeve (1982), causing the barbs (1964) to be forced toward one another. When the barbs (1964) have been forced sufficiently inwardly to clear ends (1988) of the main body (1980), the second spring (1966) then moves the needle hub (1965) in the direction of the activation means (1952). Thus the needle is removed from the infusion device leaving the infusion device in place on the skin while the retainer body remains in a position adjacent the open end of the sleeve so that once the insertion device is removed from the skin of the patient, the retainer body protects the patient from further contact with the needle.

This insertion device is rather complex and the length of the device is defined by the individual units forming the functional parts of the device as these units have to be placed more or less end to end. A feature illustrating the complexity of the unit is the fact that the two springs respectively biases the housing from the lock member and the retainer body from the needle hub while a main body is placed between the two spring systems to transfer the force from the first spring to the second spring.

According to the present invention the two spring units work directly together, as the first spring unit directly affects the movement of the carrier body while the second spring system is directly affected by the movement of the carrier body. That the spring units directly affect or is directly affected by the carrier body means that the spring units are connected to the carrier body directly or through a part which transfers the power either unchanged or under controlled modifications.

DESCRIPTION OF INVENTION

The object of the invention is to provide a simple, non-expensive inserter for an infusion device which inserter would be easy and safe for the user to handle during use and safe to dispose of after use.

The invention concerns an inserter for a medical device comprising two elastic elements where activation of the first elastic element cause a penetrating member to be inserted sub- or transcutaneously into the skin of a patient, and the second elastic element cause the penetrating member to be retracted from the skin of the patient wherein the first elastic element is in an unloaded state before activation and upon activation the first elastic element energizes the second elastic element. That the first elastic element is in an unloaded state means that it is un-biased or slightly biased, and only upon activation the first elastic element will be loaded. This assures that the first elastic element does not decay during storing before use.

According to this invention the first elastic element has two functions, it injects the penetrating member together with the medical device and it energizes the second elastic element thereby make it possible for the second elastic element to cause a retraction of the penetrating member and leaving the medical device on the patients skin.

According to one embodiment of the invention the first elastic element is a spring having a spring constant $k_1$.

According to the above embodiment of the invention or another embodiment the second elastic element is a spring having a spring constant $k_2$.

According to one embodiment of the invention the spring constant $k_1$ of the first elastic element is larger than the spring constant $k_2$ of the second elastic element, normally the spring constant $k_1 \geq 2 \times k_2$.

According to one embodiment the spring constant $k_1 \geq 0.2$ and the spring constant $k_2 \geq 0.09$.

According to one embodiment the first elastic element and/or the second elastic element are/is a helical spring.

According to one embodiment of the invention the inserter comprises
- a stationary part (10) being stationary in relation to the patient during insertion and resting against the patients skin,
- activation means (1),
- a carrier body (2) which carrier body (2) has a forward and a retracted position relative to the stationary part (10) and
- a needle hub (6) connected with a penetrating member (6A),
- first locking means (4) locking the carrier body (2) in a retracted position,
- first release means (13A) unlocking the carrier body (2) from a retracted position,
- second locking means (8, 9) locking the needle hub (6) in a forward position relative to the carrier body (2),
- second release means (15A) unlocking the needle hub (6) from the forward position, wherein the first elastic element (11) apply force to a surface of the house (1) and to a surface of the carrier body (2) and the second elastic element (12) apply force to a surface of the needle hub (6) and to a surface of the stationary part (10).

According to such an embodiment the house can be the activation means and inside the house the carrier body moves from a retracted to a forward position when the first elastic element is activated.

According to such an embodiment the second release means automatically releases the needle hub from the carrier body when it passes a certain position e.g. the release means can be part of the stationary part.

According to this embodiment a first integrated part comprising the first elastic element can be separated from a second integrated part comprising the second elastic element and the penetrating needle e.g. the first integrated part is reusable and the second integrated part is disposable.

The invention also relates to use of an inserter as described above e.g. for sub- or transcutaneously positioning of a unit for metering a substance e.g. the glucose content of the blood and/or sub- or transcutaneously positioning of an infusion part of an infusion set for delivering of a drug e.g. insulin to the patient and/or sub- or transcutaneously positioning of a gateway for replacing multiple injections.

DESCRIPTION OF THE DRAWINGS

The invention is explained in greater detail below with reference to the accompanying drawings wherein a preferred embodiment of the invention is shown.

Figures 1A, 1B:
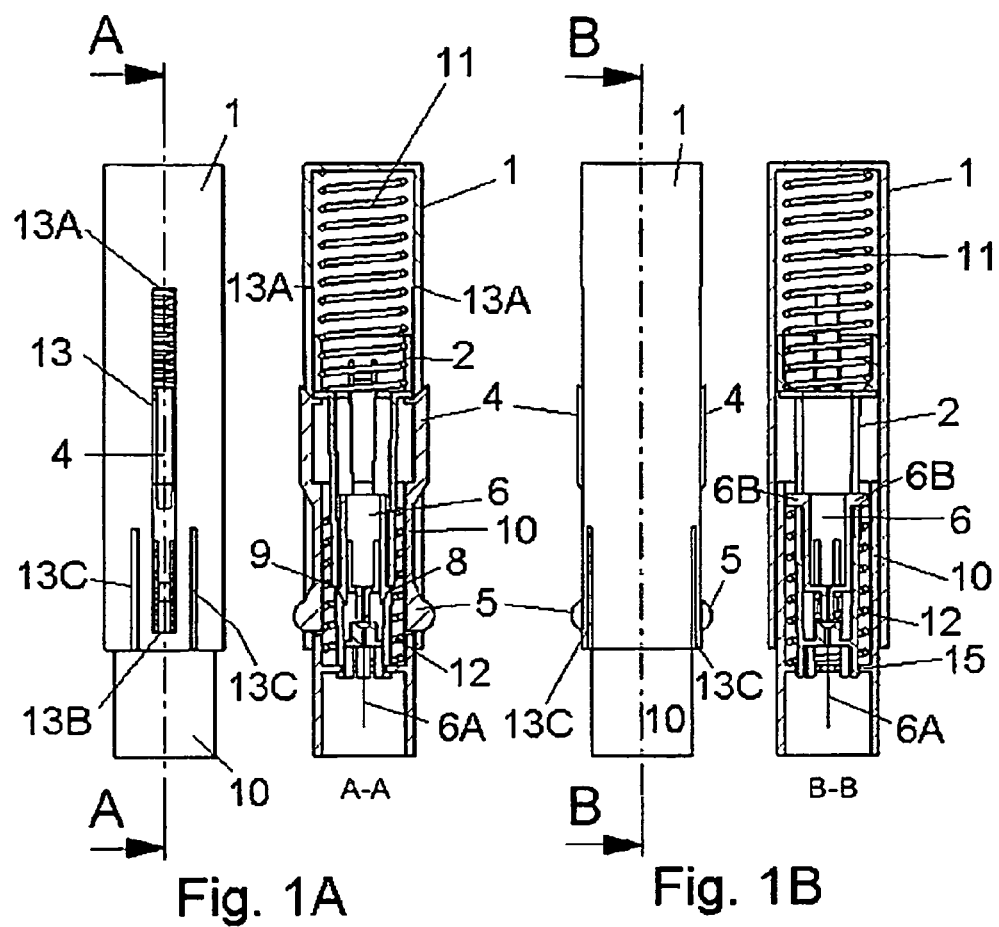
FIGS. 1A and 1B show a side view of the embodiment where the carrier body and the medical device are in a retracted position before insertion.
Figure 1C:
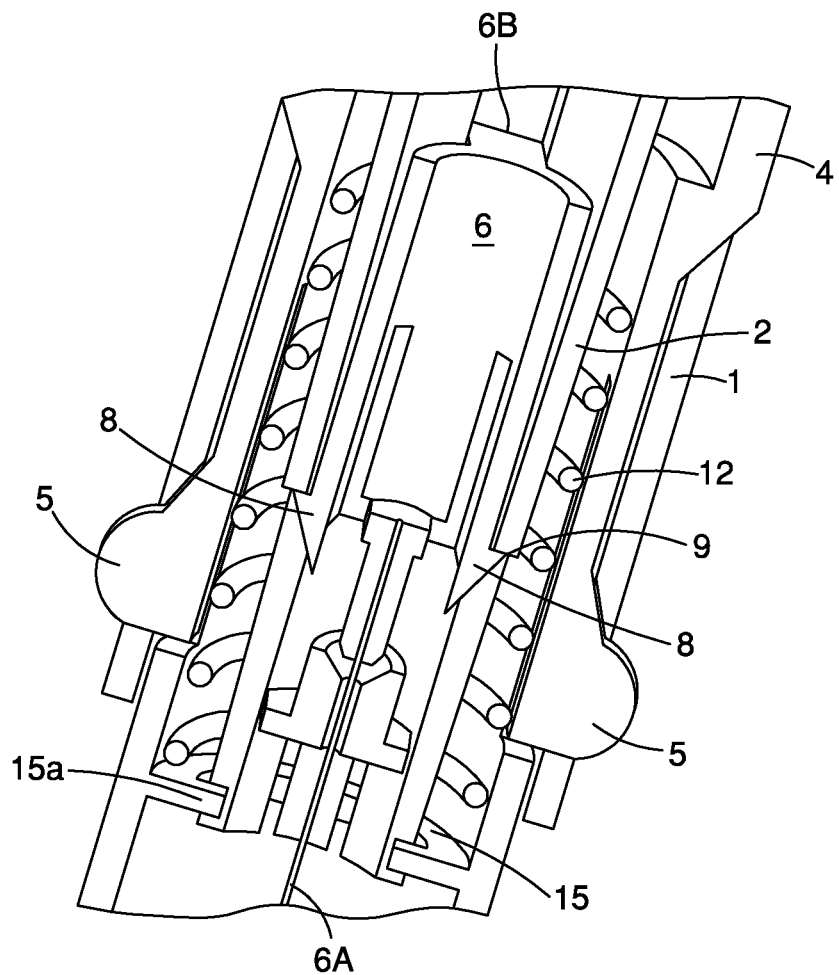
FIG. 1C shows a spatial side view of the same position.

The embodiment of the inserter device of FIGS. 1A, 1B and 1C is shown in a state before insertion of the medical device. The embodiment comprises a house 1, a carrier body 2, a stationary part 10 which is stationary in relation to the patient during use and a needle hub 6 provided with a penetrating member 6A. Further the inserter device comprises two elastic elements in the form of two spring units, an inserter spring 11 having a spring constant $k_1$ and a retraction spring 12 having a spring constant $k_2$.

The inserter spring 11 applies pressure to the house and to the carrier body 2, i.e. when the inserter spring 11 is reduced in length it exercises a pressure upwards on the house 1 and downwards on the carrier body pushing the two parts away from each other. The retraction spring 12 applies pressure to the needle hub 6 and to the stationary part 10, i.e. when the retraction spring 12 is reduced in length it exercises a pressure upwards on the needle hub 6 and downwards on the stationary part 10 (upwards/downwards relate to the embodiments as shown in the figures).

The house 1 has a cylindrical body with a closed distal end and an open proximal end, and the house 1 is provided with two longitudinal openings 13 on opposite sides of the body of the house 1; the openings are limited towards the distal end by an edge 13A and towards the proximal end by and edge 13B. Further the house 1 is provided with four slots 13C, one on each side of each longitudinal opening 13, extending from the proximal edge of the house 1.

The stationary part 10 also has a cylindrical body which fits inside the body of the house 1. The stationary part 10 comprises a pair of oppositely positioned outward arms 4 placed at the distal end of the cylindrical body and means for releasing of a replaceable part of the inserter device in the form of a pair of inward arms 5 placed closer to the proximal end of the body of the stationary part 10 than the outward arms 4. Also the stationary part 10 is provided with a protruding circular edge 15 having protruding parts 15A.

The lower or proximal side of the protruding parts on the arms 5 provides a stop for the relative movement between the stationary part 10 and the house 1, i.e. it is not possible to pull the stationary part 10 out of the house 1 when the oppositely placed arms 5 are in a relaxed position. When the arms 5 are pushed towards each other the arms 5 are in a tensioned position and it is possible to pull the stationary part 10 out of the house 1 and replace the stationary part 10 with a new e.g. unused part or e.g. with a part having another function or having a different medical device attached. The slots 13C allow an increment of the diameter of the house 1 which increment makes it possible to remove the stationary part 10 from the shown embodiment of the house 1 without destroying the house 1. After use the carrier body 2 of the embodiment shown in the figures will be stuck inside the stationary part 10, and therefore the carrier body 2 will be removed together with the stationary part 10.

The carrier body 2 also comprises a cylindrical body, where the distal end of the cylindrical body has an increased diameter compared to the proximal end of the cylindrical body. The distal part of the cylindrical part of the carrier body has a surface against which the inserter spring 11 rests, also the outward arms 4 of the stationary part 10 rest against a surface of the carrier body 2. The carrier body 2 is provided with two longitudinal openings 7 on opposite positions on the proximal part of the cylindrical body which openings functions as guiding means for protruding parts 6B of the needle hub 6. The longitudinal openings assure that the needle hub 6 can only travel a certain distance corresponding to the openings 7 inside the carrier body 2. The carrier body 2 also is provided with a closed proximal exit having an opening which is just large enough to allow the penetrating member to pass through. Such a nearly closed end prevents access to the contaminated penetrating member after use. The embodiment shown in the figures also has two openings 7A perpendicular to the openings 7 and extending from the proximal end of the cylindrical body of the carrier body 2. The protruding parts 15A of the protruding circular edge 15 of the stationary part 10 extend into these openings 7A and are guided along the openings 7A when the carrier body 2 moves in relation to the stationary part 10. The proximal end surface of the carrier body 2 touches the patient's skin when the carrier body 2 is in a most forward position relative to the stationary part 10. When the carrier body 2 is in a most retracted position relative to the stationary part 10—which is the state shown in FIGS. 1A, 1B and 1C—, inward protruding parts of the outward arms 4 of the stationary part 10 rest against a surface of the distal part of the cylindrical body of the carrier body 2.

The needle hub 6 is before use placed inside the distal part of the cylindrical body of the carrier body 2. The distal end of the needle hub 6 is provided with two protruding parts 6B which are placed on opposite positions on the cylindrical body of the needle hub 6 (shown in FIG. 1B) and as mentioned above the longitudinal openings 7 assure that the needle hub 6 can only travel a certain distance inside the carrier body 2 corresponding to the length of the openings 7. The needle hub also comprises pivotally mounted arms 8 having hooks which in the retracted position are in contact with proximal turned surfaces 9 of the carrier body 2. This proximal turned surface 9 is the distal edge of the opening 7A.

Figures 2A, 2B:
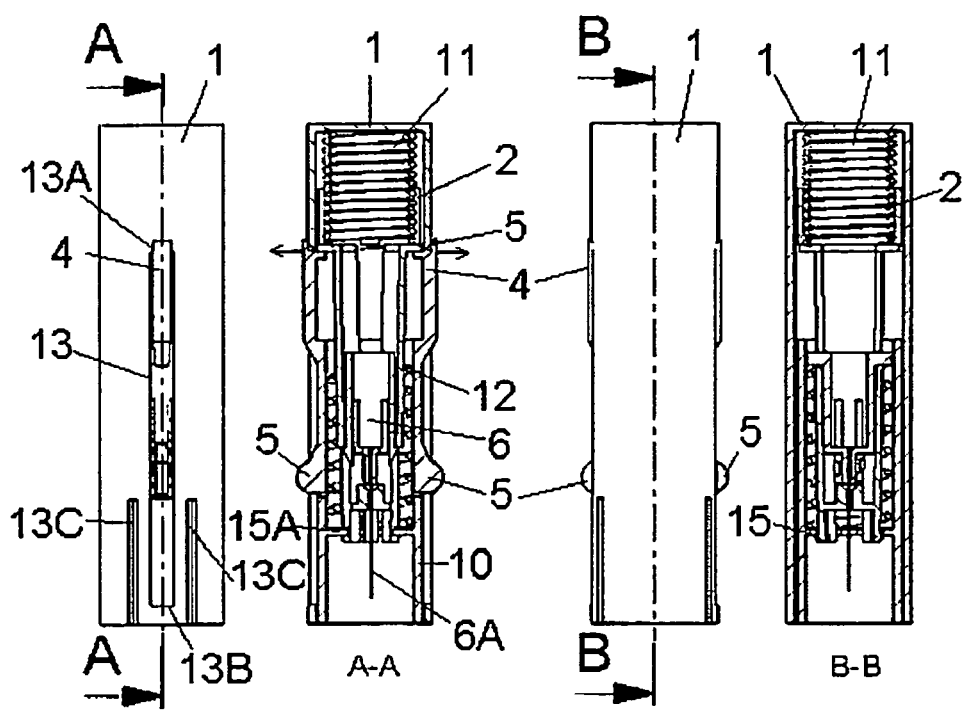
FIGS. 2A and 2B show a side view of the embodiment where the carrier body and the medical device are in a retracted position before insertion.
Figure 2C:
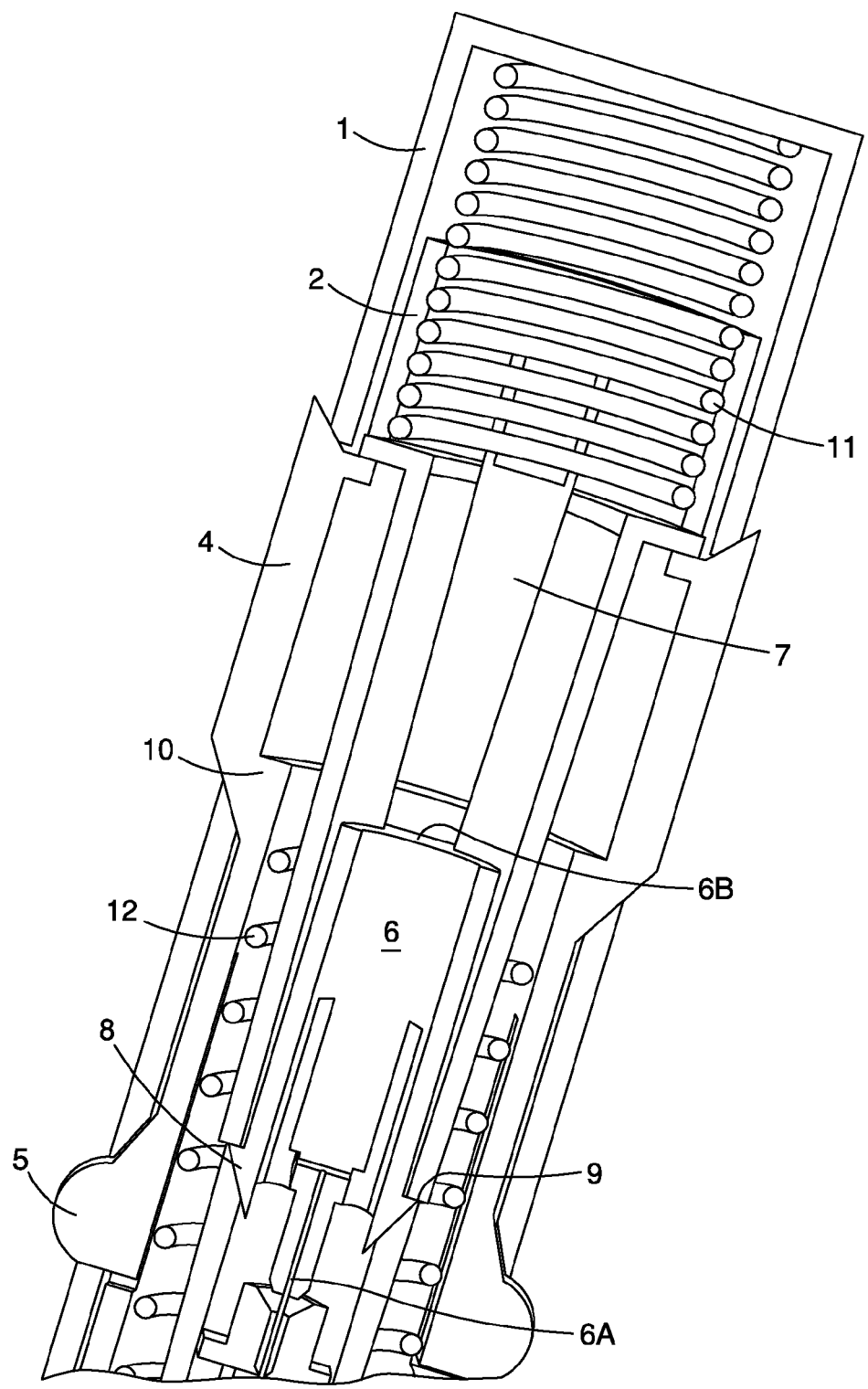
FIG. 2C shows a spatial side view of the same position.

FIGS. 2A, 2B and 2C show the inserter device in a state where the inserter spring 11 is compressed and therefore biased but before the carrier body 2 and the needle hub 6 is brought forward.

As indicated with arrows in FIG. 2A the outward arms 4 of the stationary part 10 is affected by an outward pressure which pressure results from the contact between the outward arms 4 and the proximal edge 13A of the opening 13. When the inclined surface of the outward arms 4 slides against the distal edge 13A of the opening 13 in the house 1 the contact causes the arms 4 to be moved away from each other. When the outward arms 4 of the stationary part 10 is freed from contact with the distal edge 13A of the opening 13, then the compressed inserter spring 11 will exercise a downward force on the carrier body 2 and on the needle hub 6 which at this point is locked to the carrier body 2.

Figures 3A, 3B:
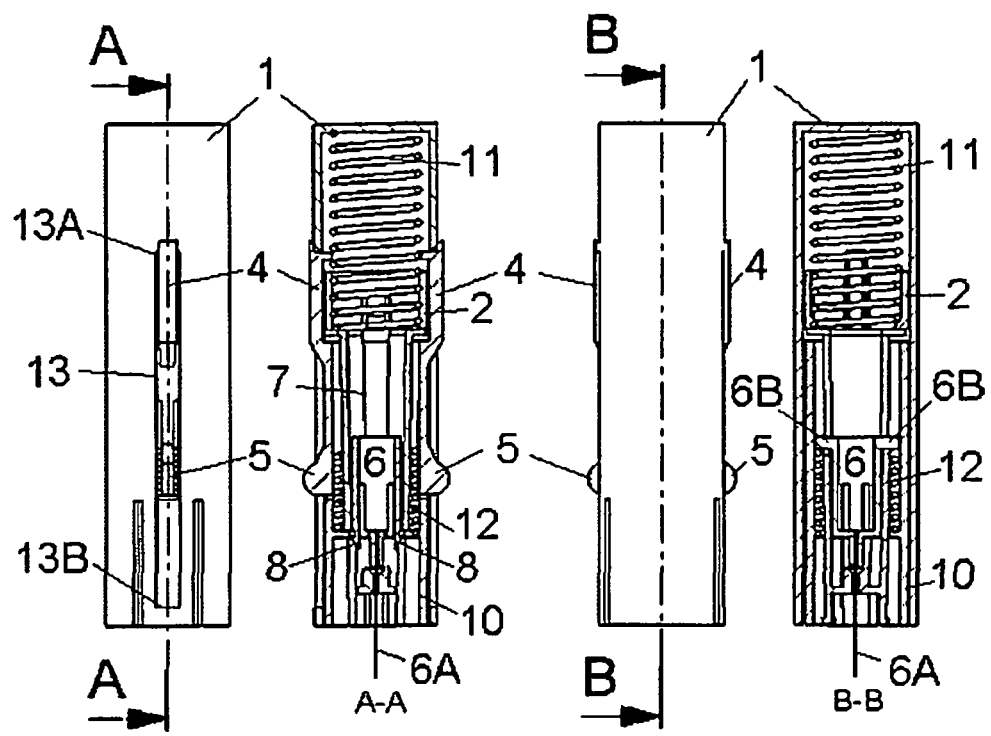
FIGS. 3A and 3B show a side view of the embodiment where the carrier body and the medical device are in a fully forward position.
Figure 3C:
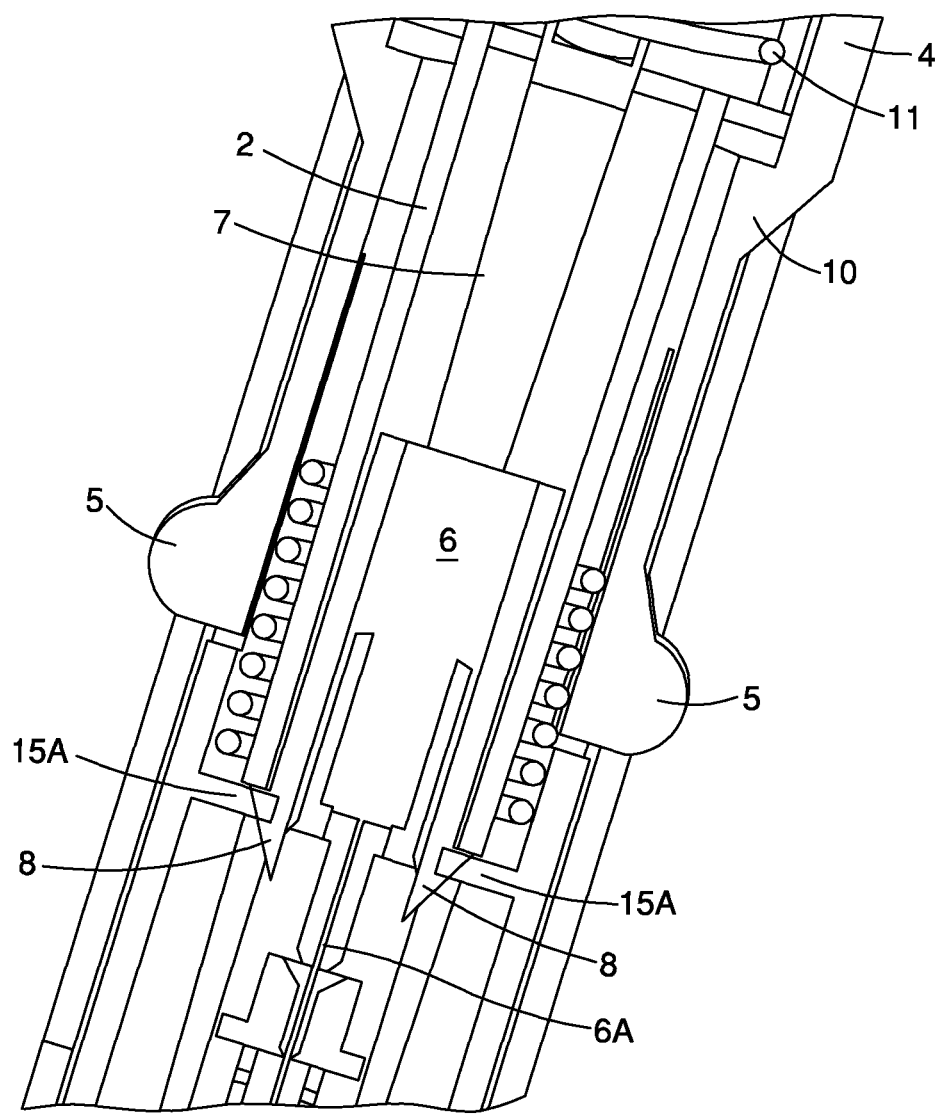
FIG. 3C shows a spatial side view of the same position.

The downward movement of the combined carrier body and needle hub 6 brings the inserter device to the state illustrated in FIGS. 3A, 3B and 3C.

FIGS. 3A, 3B and 3C shows the needle hub 6 in a position where the penetrating member 6A is fully inserted in the patients skin. The retraction spring 12 has been compressed and thereby energized as the spring constant $k_2$ of the retraction spring 12 which pushes upward on the protruding parts 6B of the needle hub 6 is smaller than the spring constant $k_1$ of the inserter spring 11 which pushes downward on the carrier body 2. Normally the spring constant $k_1$ of the inserter spring 11 is equal to or larger than 0.25 N/mm and the spring constant $k_2$ of the retraction spring 12 is equal to or larger than 0.1 N/mm. After the distal part of the cylindrical body of the carrier body 2 has passed between the outward arms 4 of the stationary part 10, the outward arms 4 return to their position and the distal part of the carrier body 2 is now between the arms 4 instead of above the arms 4 as shown in FIG. 2. The carrier body 2, the stationary part 10 and the house 1 are at this position all at a level where they touch the patients skin. The pivotally mounted arms 8 of the needle hub 6 which have an inclined surface have in this position been forced inwards by the protruding parts 15A of the protruding circular edge 15. The inward movement is a result of the stationary protruding parts 15A touching the pivotally mounted arms 8 when the arms 8 move downwards.

Figures 4A, 4B:
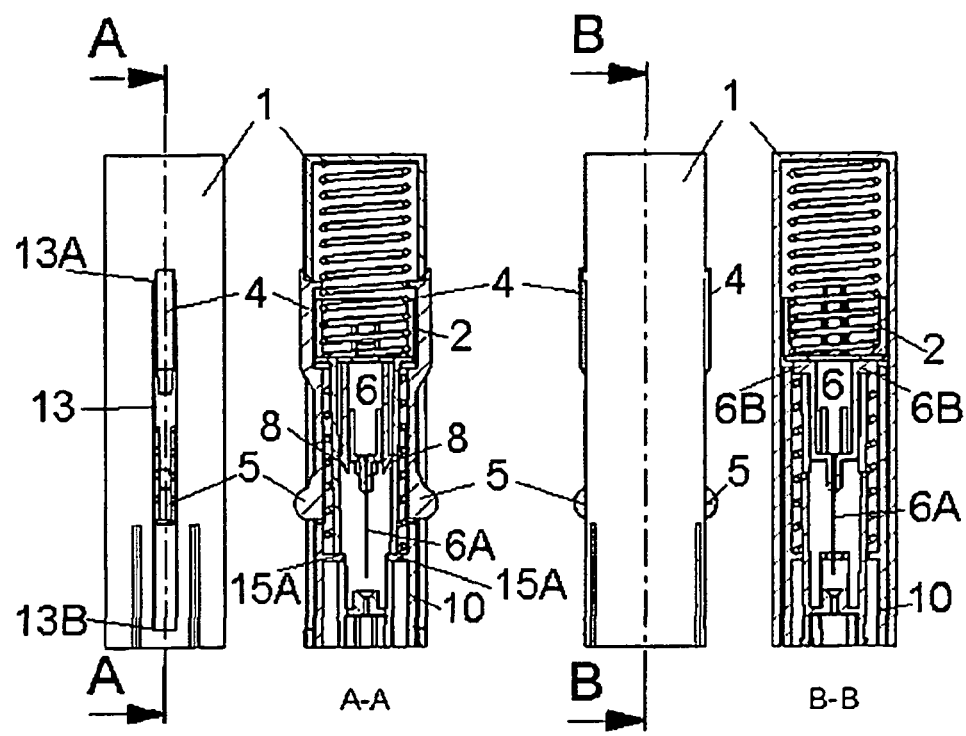
FIGS. 4A and 4B show a side view of the embodiment where the carrier body is in a forward position and the medical device is in a retracted position.
Figure 4C:
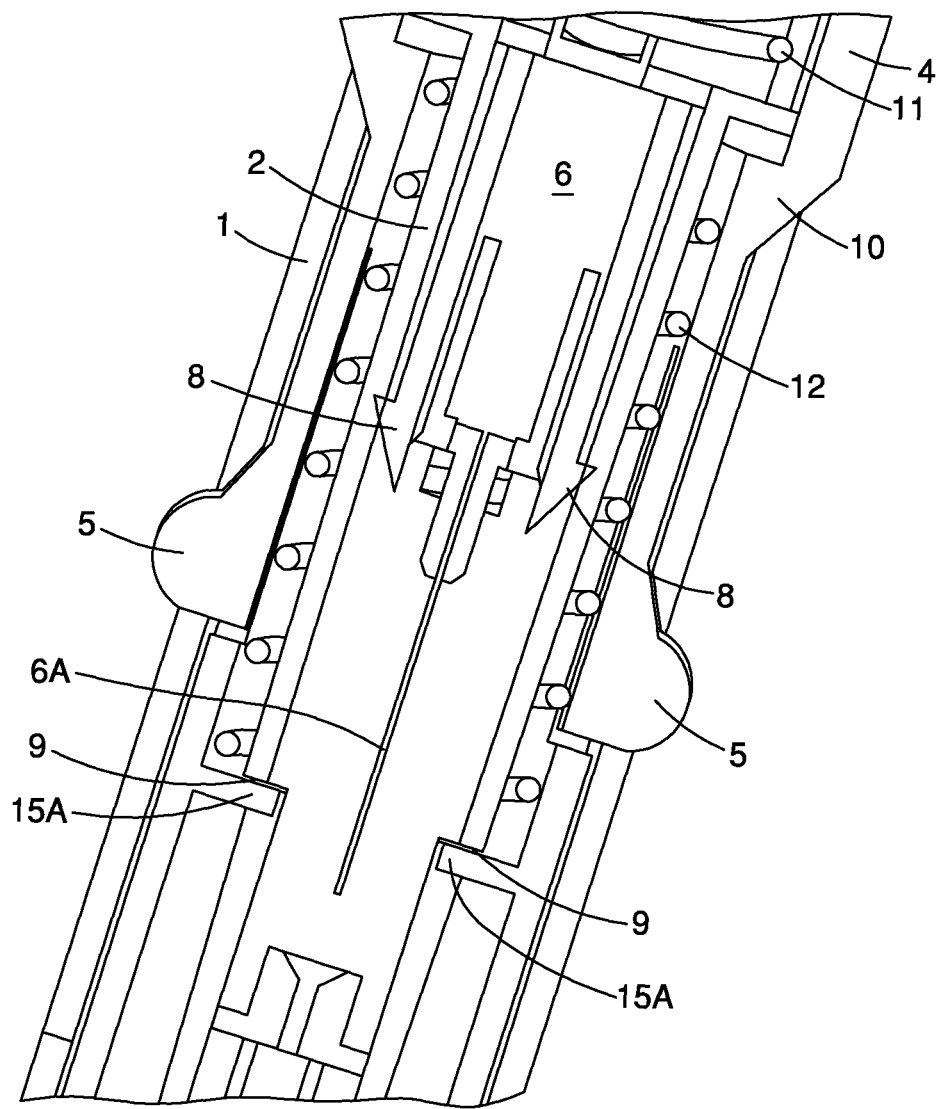
FIG. 4C shows a spatial side view of the same position.

FIGS. 4A, 4B and 4C shows the inserter device in a state where the needle hub 6 is in a position where the penetrating member 6A is fully retracted from the patients skin. The retraction spring 12 has pushed the needle hub 6 as far upwards and away from the patient as possible, the needle hub 6 can only move to the upper end of the proximal part of the carrier body 2 as the protruding parts 6B of the needle hub 6 at this position will come into contact with a surface of the distal part of the carrier body 2.

Figures 5A, 5B:
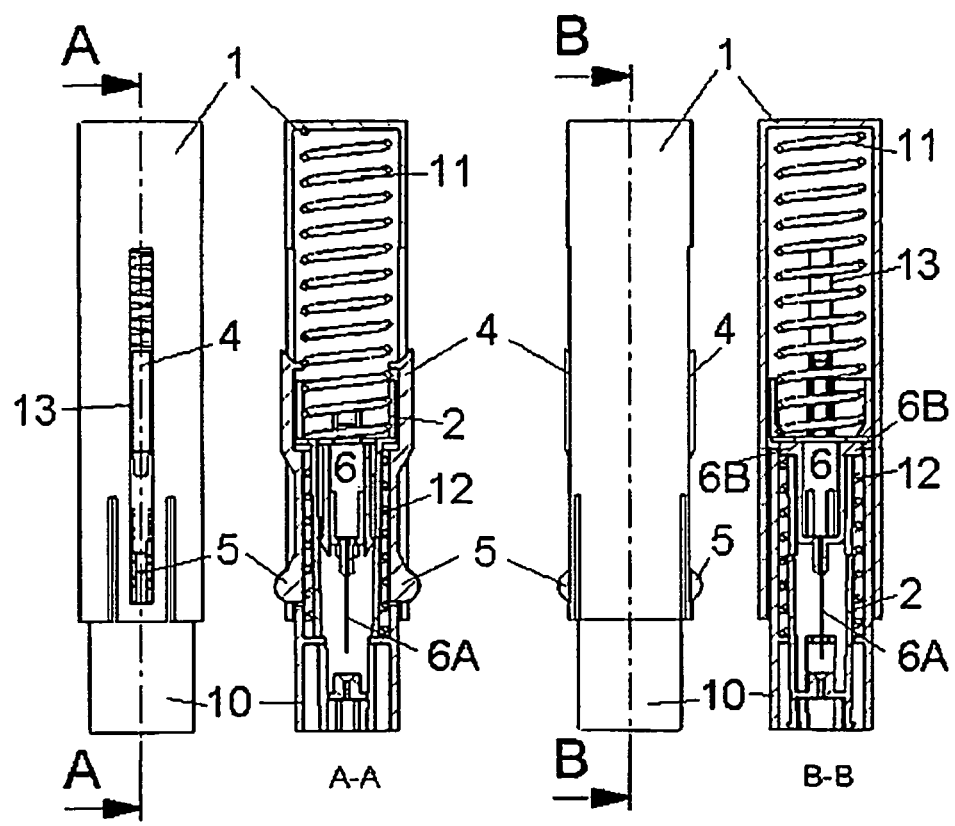
FIGS. 5A and 5B show a side view of the embodiment where the carrier body and the medical device are in a retracted position after insertion.
Figure 5C:
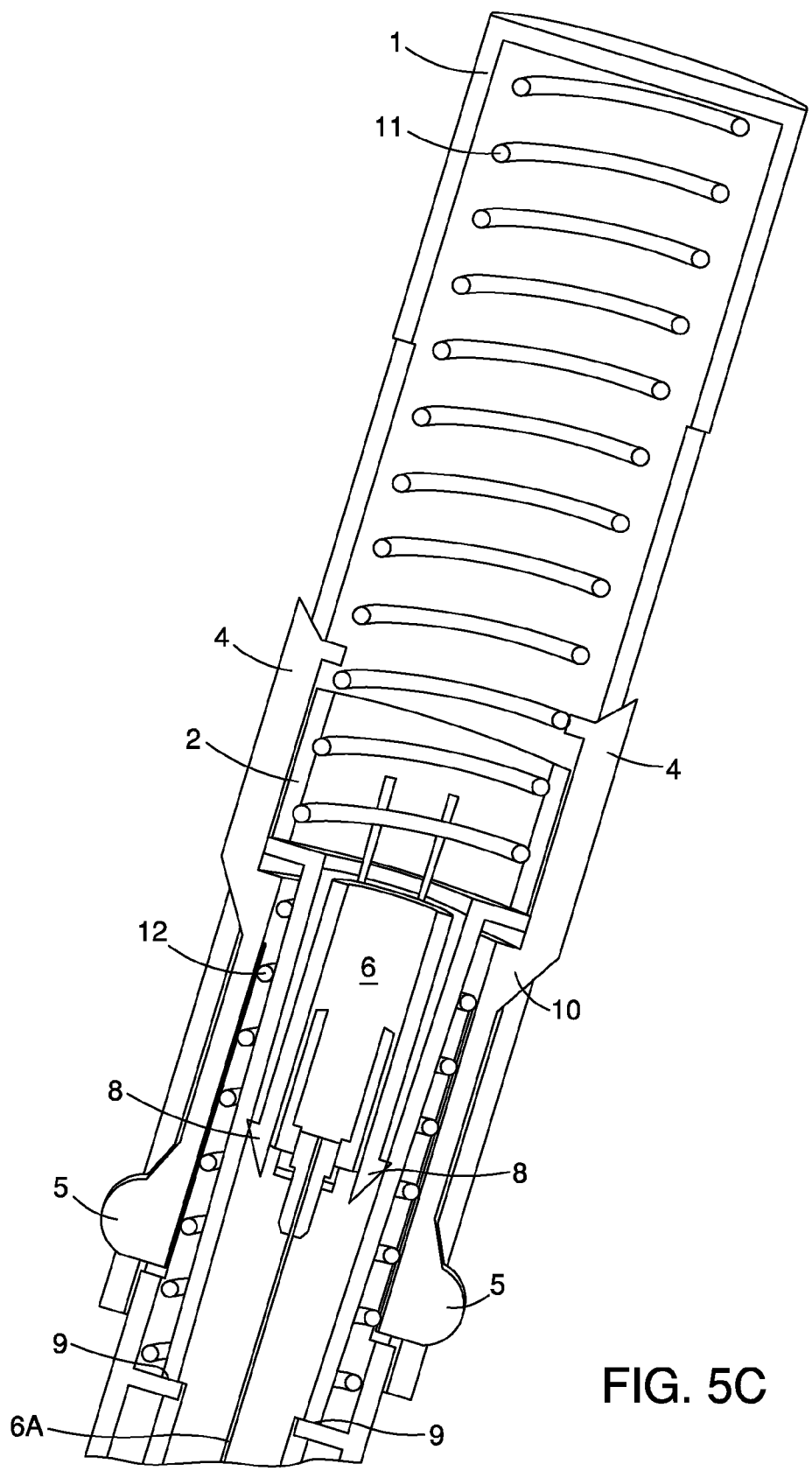
FIG. 5C shows a spatial side view of the same position.

FIGS. 5A, 5B and 5C shows the inserter device in a state where the needle hub 6, the carrier body 2 and the stationary part 10 are positioned as in FIG. 4, but in FIG. 5 the user has released the pressure on the house 1 and therefore the house has jumped back into the same position as in FIG. 1 where the inserter spring 11 is relaxed.

When using the inserter device a medical device, which is not shown on the drawings, is placed on or in connection with the penetrating member 6A either inside the stationary part 10 if e.g. the medical device has a diameter smaller than the inner circumference of the stationary part 10 or it is placed partly inside and partly around the proximal end of the stationary part 10 if the diameter of the medical device is larger than the inner circumference of the stationary part 10.

Figure 6:
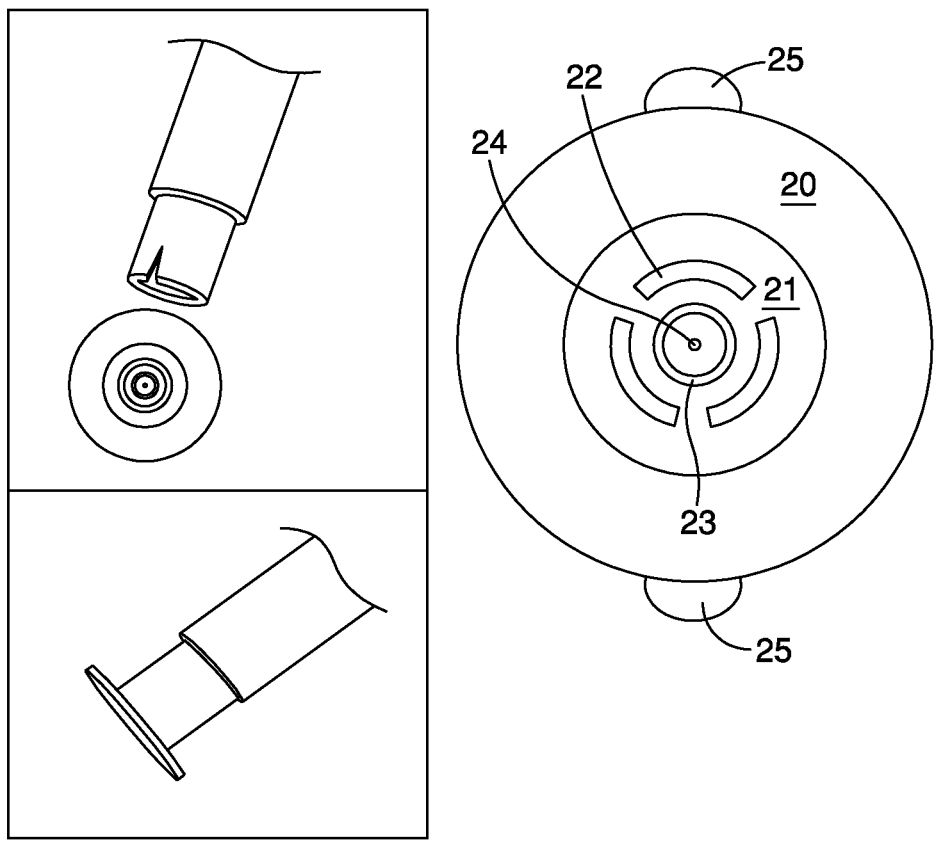
FIG. 6 shows a top view of a medical device which can be used with the inserter device.

FIG. 6 shows a top view of a medical device which can be used in the inserter device shown in FIG. 1-5. The medical device is of the port type and therefore only provides an access to the patients blood e.g. with a syringe without having to penetrate the patients skin again and again. The medical device comprises a mounting pad 20 having an adhesive surface which is normally covered by a protective release layer. The only parts of the release layer which are being visible on FIG. 6 are the handle parts 25, which are used to remove the release layer just before use. Further the medical device comprises a body 21 provided with tracks 22 for mounting of the stationary device 10, tracks 23 for allowing entrance of the carrier body 2 and a through-going opening 24 for the penetrating member 6A of the needle hub 6. The shown embodiment has three partly circular tracks 22 which correspond to protruding end parts on the stationary part 10. A close fitting between the tracks 22 and the protruding parts of the stationary part 10 will normally be enough to hold the medical device in position on the stationary part before insertion. The body 21 of the medical device is also provided with a circular track 23 which is able to receive the proximal end of the carrier body 2. When the carrier body 2 is moved forward towards the patients skin the carrier body 2 enters the tracks 23, the tracks 23 do not need to have a close fit to the proximal end of the carrier body 2, the tracks 23 merely has to provide a guidance in order for the penetrating member 6A to enter at exactly the right position i.e. the through-going opening 24.

If the medical device is provided with a cannula extending from the proximal side of the device, the medical device has to be fastened to the inserter device before insertion in order to have the cannula mounted subcutaneously and in this case the medical device will either be mounted in such a way that the penetrating member 6A of the needle hub 6 is placed inside a soft cannula when the inserter device and the medical device are delivered to the user, or the if the medical device is provided with a hard self-penetrating cannula then the medical device can be delivered to the user connected to the needle hub 6 or the user can unpack the sterile medical device and connect it to the needle hub 6.

If the medical device is not provided with a cannula, then the medical device can be fastened to the patients skin before insertion. The cannula will then—irrespective of whether this is a hard self-penetrating or a soft cannula—be provided together with the needle hub 6 e.g. as a separate cannula part (1*b*) as shown in PCT application no. PCT/DK2006/000737.

If the medical device is provided with a soft cannula, the medical device will be delivered to the patient as an integrated part of the inserter device. When the inserter device has been unpacked and is ready for use the release layer is removed from the mounting pad 20 and then the medical device joint to the inserter device is placed against the skin of the patient. The user then activates the insertion procedure by pushing the house 1 of the inserter device towards the patients skin. This one push causes the needle hub and the hereto joint medical device and penetrating member 6A to be inserted subcutaneously and afterwards the penetrating member 6A is automatically being retracted and placed inside the carrier body 2. The user can then remove the inserter device from the medical device leaving the medical device fully functional on the patients skin.

The inserter might be constructed having a first integrated part comprising a group of elements which can be reused. This first integrated part will normally comprise the house 1 which then can be made more durable and be provided with a more luxurious and expensive look and details. Normally this first integrated part will also comprise the first elastic element 11 as this element could then be constructed in a more expensive quality. The first integrated part would be combined with a group of elements in the form of a second integrated part which part cannot be reused. The second integrated part would e.g. comprise the insertion needle and parts combined with the insertion needle e.g. the second elastic element.

The inserter can be used for sub- or transcutaneously positioning of a unit for metering a substance e.g. the glucose content of the blood and/or for sub- or transcutaneously positioning of an infusion part of an infusion set for delivering of a drug e.g. insulin to the patient and/or sub- or transcutaneously positioning of a gateway for replacing multiple injections, such a gate way is e.g. known from the international patent application PCT/DK2006/050005 and this gateway is incorporated in the present application by reference. The inserter can also be used for inserting a cannula device as known from PCT/DK2006/00737 e.g. FIGS. 32-36, such a cannula device is hereby incorporated in the present application by reference.

| List of references: | |
|---|---|
| House | 1 |
| Carrier body | 2 |
| Outward arms of stationary part | 4 |
| Inward arms of stationary part | 5 |
| Needle hub | 6 |
| Penetrating member | 6A |
| Protruding parts of needle hub | 6B |
| Longitudinal opening in carrier body | 7 |
| Openings perpendicular to the openings 7 in the carrier body 2 | 7A |
| Pivotally mounted arms of needle hub | 8 |
| Proximal turned surface of carrier body | 9 |
| Stationary part | 10 |
| Inserter spring F1 | 11 |
| Retraction spring F2 | 12 |
| Longitudinal opening in house | 13 |
| Distal edge of opening in house | 13A |
| Proximal edge of opening in house | 13B |
| Slots in house | 13C |
| Pivotally arms of needle hub | 14 |
| Protruding circular edge of stationary part | 15 |
| Protruding parts of protruding circular edge | 15A |
| Mounting pad | 20 |
| Body of medical device | 21 |
| Tracks for stationary part in medical device | 22 |
| Opening in medical device for receiving carrier body | 23 |
| Through-going opening for penetrating member | 24 |
| Handle parts of release layer | 25 |

The invention claimed is:

1. An inserter for a medical device comprising:
a stationary part being stationary in relation to the patient during insertion and resting against the patient's skin;
a carrier body having a forward and a retracted position relative to the stationary part;
a needle hub connected with a penetrating member;
a first elastic element and a second elastic element configured such that activation of the first elastic element causes a penetrating member to be inserted sub- or transcutaneously into the skin of a patient, and the second elastic element causes the penetrating member to be retracted from the skin of the patient, the first elastic element is in an unloaded state before activation and upon activation, the first elastic element energizes the second elastic element;
a first locking member configured to releasably lock the carrier body in the retracted position;
a first release member configured to unlock the carrier body from the retracted position;
a second locking member configured to releasably lock the needle hub in a forward position relative to the carrier body;
a second release member configured to unlock the needle hub from the needle hub forward position, the needle hub being movable relative to the carrier body; and
an activator configured to activate the first elastic element.

2. An inserter for a medical device according to claim 1, wherein the second release member automatically releases the needle hub from the carrier body when the second release member passes a release position.

3. An inserter for a medical device according to claim 2, wherein the release member is part of the stationary part.

4. An inserter for a medical device according to claim 1, wherein the second locking member comprises pivotally mounted arms having hooks, the hooks contacting proximal turned surfaces of the carrier body in the retracted position.

5. An inserter for a medical device according to claim 4, wherein the pivotally mounted arms having an inclined surface are forced inwards by protruding parts of a protruding circular edge in a position where at least a portion of the carrier body, the stationary part and a housing contact the patient's skin.

6. An inserter for a medical device according to claim 1, wherein the medical device to be inserted is either provided with a cannula extending from a proximal side of the device.

7. An inserter for a medical device according to claim 6, wherein the cannula can be a soft cannula or a hard self-penetrating cannula.

8. An inserter for a medical device according to claim 1, wherein the first elastic element is a spring having a spring constant $k_1$ and the second elastic element is a spring having a spring constant $k_2$.

9. An inserter for a medical device according to claim 8, wherein $k_1 \geq 2k_2$.

10. An inserter for a medical device according to claim 7, wherein the spring constant $k_1$ of the first elastic element is larger than the spring constant $k_2$ of the second elastic element.

11. An inserter for a medical device according to claim 8, wherein the spring constant $k_1 \geq 0.2$ and the spring constant $k_2 \geq 0.09$.

12. An inserter for a medical device according to claim 1, wherein the first elastic element or the second elastic element is a helical spring.

13. An inserter for a medical device according to claim 1, wherein the first elastic element is configured to apply force to a surface of a housing and to a surface of the carrier body and the second elastic element is configured to apply force to a surface of the needle hub and a surface of the stationary part.

14. An inserter for a medical device according to claim 13, wherein the housing is the activator and inside the housing, the carrier body moves from the retracted to the forward position when the first elastic element is activated.

15. An inserter for a medical device according to claim 14, wherein a first integrated part comprising the first elastic element can be separated from a second integrated part comprising the second elastic element and the penetrating needle.

16. An inserter for a medical device according to claim 15, wherein the first integrated part is reusable and the second integrated part is disposable.

17. An inserter for a medical device according to claim 1, wherein the medical device comprises a unit for metering a substance, an infusion part of an infusion set for delivering of a drug or a gateway for replacing multiple injections.

18. A method of sub- or transcutaneously position a medical device, the method comprising:
   providing an inserter according to claim 1; and
   sub- or transcutaneously positioning the medical device using the inserter; and
   metering a substance, delivering a drug or combinations thereof.

19. The method of claim 18, comprising fastening a medical device to a patient's skin and sub- or transcutaneously positioning a separate cannula part using the inserter.

\* \* \* \* \*